United States Patent [19]
Jacobs

[11] Patent Number: 4,750,492
[45] Date of Patent: Jun. 14, 1988

[54] ABSORBABLE SUTURE APPARATUS, METHOD AND INSTALLER

[75] Inventor: Randall W. Jacobs, Memphis, Tenn.

[73] Assignee: Richards Medical Company, Memphis, Tenn.

[21] Appl. No.: 706,006

[22] Filed: Feb. 27, 1985

[51] Int. Cl.⁴ .............................................. A61B 17/08
[52] U.S. Cl. ................................... 128/335; 128/335; 128/334 R; 128/326
[58] Field of Search ............... 128/334 R, 334 C, 335, 128/325, 326

[56] References Cited

U.S. PATENT DOCUMENTS

| | | | |
|---|---|---|---|
| 462,270 | 11/1891 | McConnaughey | 128/334 R |
| 1,461,524 | 7/1923 | Goddard | 128/334 R |
| 1,669,537 | 5/1928 | Schaffer | 128/334 R |
| 3,409,014 | 11/1968 | Shannon | 128/326 |
| 3,541,591 | 11/1970 | Hoegerman | 128/335 |
| 3,802,438 | 4/1974 | Wolvek | 128/335 |
| 3,831,608 | 8/1974 | Kletschka et al. | 128/335 |
| 3,857,396 | 12/1974 | Hardwick | 128/335 |
| 3,910,281 | 10/1975 | Kletschka et al. | 128/335 |
| 4,016,883 | 4/1977 | Wright, Jr. | 128/325 |
| 4,291,698 | 9/1981 | Fuchs et al. | 128/335 |

FOREIGN PATENT DOCUMENTS 820812  4/1981  U.S.S.R. .......................... 128/92 BC

Primary Examiner—C. Fred Rosenbaum
Assistant Examiner—Colleen Reilly
Attorney, Agent, or Firm—Pravel, Gambrell, Hewitt, Kimball & Krieger

[57] ABSTRACT

An apparatus for repairing torn animal body tissue in a single procedure features a suture, anchor attached at one end of the suture to prevent the suture from being pulled through the tissue, and clenching device adapted to grip the suture on the opposite side of the tissue from where the anchor device is disposed so that the torn tissue may be held together by cooperating between the anchor device and the clenching device within the body, all of which are formed of a biodegradable material so that they will all be absorbed into the body over time thereby eliminating the need for another surgical procedure to remove them from the body. The installer is used to install the clenching device with one hand so that the other is free to pull on the suture.

5 Claims, 2 Drawing Sheets

U.S. Patent  Jun. 14, 1988  Sheet 1 of 2  4,750,492
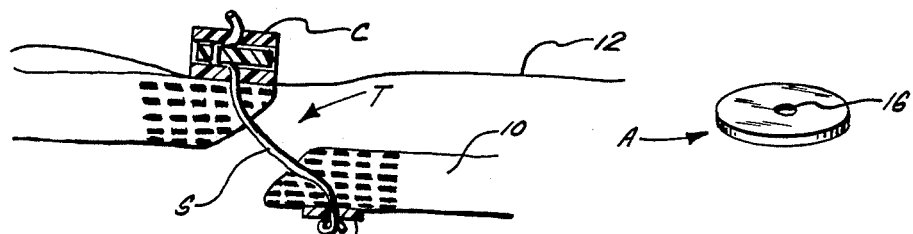
FIG. 1.
FIG. 2.
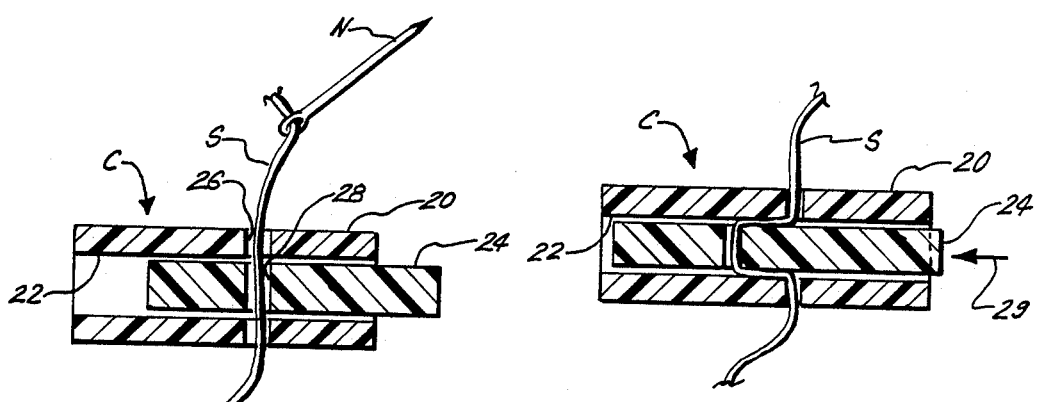
FIG. 3.
FIG. 4.
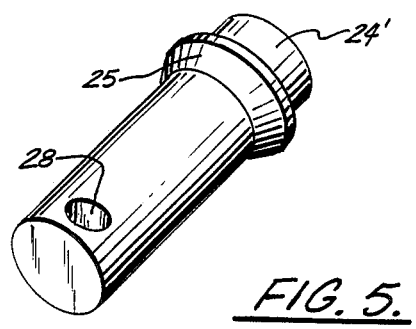
FIG. 5.
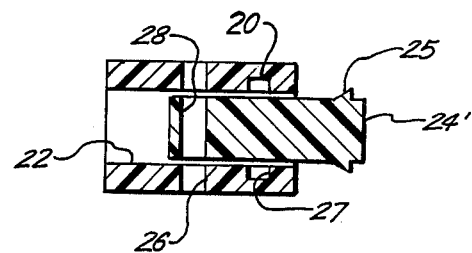
FIG. 6.

ABSORBABLE SUTURE APPARATUS, METHOD AND INSTALLER

FIELD OF THE INVENTION

This invention relates to an apparatus, method and installer for repairing torn animal body tissue in a single surgical procedure.

BACKGROUND OF THE INVENTION

A frequent injury to active people, especially athletes, involves a tear in the miniscal cartilage of the knee, especially when the leg is twisted. Such a tear is normally repaired through accepted surgical procedures where the damaged tissue is either removed or the torn edges sewn together.

For younger patients or those where the tear is small, it is often desirable to sew the tissue together and provide it with an opportunity to heal. An accepted procedure for performing this operation includes forming an incision and suturing the torn cartilage for holding it together. Typically, the suture is held in place in cartilage tissue on one side of the tear by a knot that is tied at one end or an anchor. The torn edges of the tissue are then sewn together, with the suture being tied off or secured by a button or other type of holding device located outside the joint capsule.

There are disadvantages to these procedures. First, when the suture is tied off, the surgeon must make two puncture wounds for each suture and take extra time to manipulate the suture in an awkward location and take care in making sure the tear is held together by the suture. When a suture is held by a securing device, a portion of the suture projects out of the incision while the torn cartilage is healing. Such securing devices are shown in U.S. Pat. Nos. 3,976,075; 4,291,698 and 3,664,345. Further, in order to remove the suture in either case, a second incision must be made, which tends to increase the risk for infection and prolongs the healing of the injury.

While the use of biodegradable sutures that are absorbable when they come in contact with moisture in the human body are known (see U.S. Pat. Nos. 4,208,511; 4,429,080 and 4,452,973) none is known to have been adapted for repairing torn tissue without the need for tying the suture for holding it in place in the damaged tissue or using a securing device outside the capsule.

SUMMARY OF THE INVENTION

In accordance with the invention, an apparatus, method and installer for repairing torn animal tissue in a single surgical procedure are described in detail below. The apparatus and method include the use of a suture formed of a biodegradable material in conjunction with an anchor and clenching device that are also formed of a biodegradable material. The anchor is connected at one end of the suture for preventing it from being pulled through the tissue. The clenching device is used to clench or hold the suture on the side of the tear opposite the anchor for cooperating with the anchor to hold the torn tissue together so that it can heal.

The suture, anchor and clenching device are all formed of a biodegradable material that is formulated to absorb into the patient's body after enough time has passed to allow to tear to heal; for example, 2-3 months. This latter feature eliminates the need for any portion of the apparatus from being located outside the patient's skin or another surgical procedure to remove any components of the apparatus from the patient after the injury has healed.

The installing device enables a surgeon to easily grasp the clenching device and pull the suture through it for closing the tear and then clamping the suture for holding the torn tissue together. The installing device can be operated with one hand and is easily disengagable from the clenching device after the suture is clamped. After the suture has been pulled across the tear, threaded through the clenching device in its open position and pulled tight to close the tear, a slide in the installing device is moved by the surgeon, which operates to squeeze the clenching device and clamp the suture in place. The suture is then clipped and the installing device removed from the incision. The incision is sutured in order to close the wound.

After a predetermined period of time sufficient to allow the tissue tear to heal, the anchor, suture and clenching device are absorbed into the body of the patient. In this way, a knotless way of closing the tear is provided, which eliminates the need for a second surgical procedure after the tear is healed and multiple puncture wounds for each suture.

BRIEF DESCRIPTION OF THE DRAWINGS

A detailed description of a preferred embodiment of the invention is set forth below, which, when taken with the following drawings, will provide a better understanding of the invention:

FIG. 1 is a sectional schematic view of a tear in a miniscal cartilage of the knee and shows an embodiment of the present invention for repairing the tear;

FIG. 2 is a perspective view of one type of anchor device for use in conjunction with the present invention;

FIG. 3 is a sectional view of one embodiment of a clenching device in its open position;

FIG. 4 is a sectional view of the clenching device of FIG. 3 in its closed position for clamping a suture;

FIG. 5 is a schematic view of another embodiment of the plunger portion of the clenching device of FIGS. 3 and 4 with a locking ridge;

FIG. 6 is a sectional view of the clenching device with cooperating locking ridges.

DETAILED DESCRIPTION OF A PREFERRED EMBODIMENT

Figure 7:
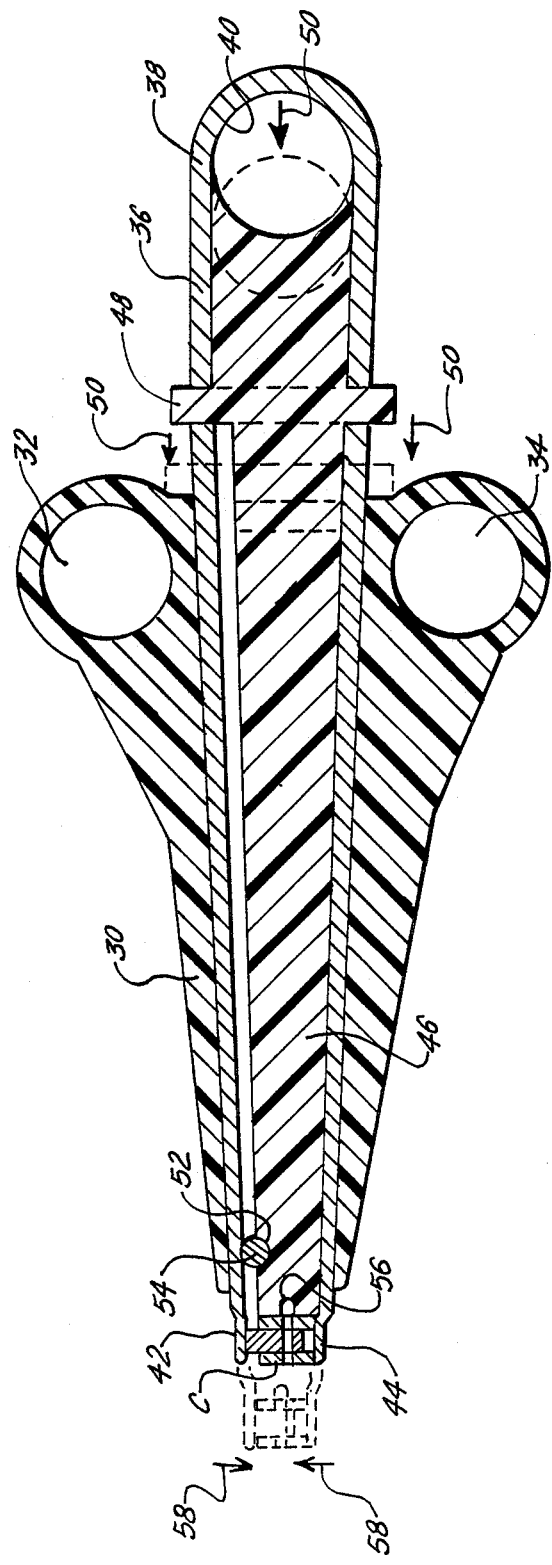
FIG. 7 is a sectional view of an instrument designed for installing the clenching device of FIGS. 3 and 4.

FIG. 1 of the drawings illustrates schematically a tear T in a miniscal cartilage 10 of a human knee that is located within a joint capsule 12, which has been closed through the use of an anchor A, suture S and a clenching or clamping device C of the present invention, all of which are formed of a suitable biodegradable material as discussed in greater detail below. Understandably, the elements of FIG. 1 are exaggerated in size and in their relative spatial relationships to better illustrate the invention.

After such a tear has been diagnosed and surgery is ready to be performed, several puncture wounds are made in the outer skin of the patient (not shown), in accordance with accepted procedures for conducting arthroscopic surgery. A knot 18, which has been formed in one end of the suture S holds the sture in place after it is threaded with an appropriate needle N through an opening 16 in the anchor A (See FIGS. 1 and 2). The anchor A is used to hold the suture in place on one side of the tear T and can be formed of a variety of shapes including toggles, beads and buttons with one or more openings. Other types of holding devices could be provided for holding the suture S in place without the need for forming the knot 18, or a knot 18 can be used to anchor the suture S without using a holding device.

The surgeon closes the tear T by threading the suture S through the portion of the miniscal cartilage 10 on one side of the tear T and then through the portion of the miniscal cartilage 10 on the other side of the tear T as shown in FIG. 1. The anchor A is positioned on the first side of the tear T as shown.

After the suture S is passed through the portion of the miniscal cartilage 10 on the other side of the tear T, it is inserted through a clenching device C such as the one shown in FIGS. 3 and 4. The clenching device C enables the surgeon to tighten the suture S for pulling the miniscal cartilage on opposite sides of the tear T together and then to clamp the suture and hold it in place until the tear can heal.

As shown in FIGS. 3 and 4, the clenching device C includes a tubular-shaped body portion 20 with an opening 22 extending longitudinally through it. A plunger 24 is formed to cooperate with the tubular opening 22, with coextensive openings 26 (in the tubular body 20) and 28 (in the plunger 24) for allowing the suture S to be threaded through the clenching device as shown in FIG. 3 and held in place when the plunger is moved relative to the tubular body in the direction of arrow 29 as shown in FIG. 4. The plunger 24 is sized relative to the opening 22 such that when the plunger is moved to the position of FIG. 4, the suture S causes a friction fit that will hold the plunger in place. Other types of clenching devices can be used provided that they can be used to clamp the suture and hold it firmly in place when the edges of the tear T are pulled together.

As shown in FIGS. 5 and 6, the plunger 24' can be provided with an annular locking ridge 25 that projects from the outer surface of the plunger 24' for cooperating with an internal locking ridge 27 formed on the inner surface of the body portion 20. The locking ridge 25 has a flared undersurface to allow it to move into the opening 22 until the ridge 25 engages the internal ridge 27 where the plunger 24' becomes locked in the body portion 20. This locking feature prevents the plunger 24' from moving relative to the body portion 20 after the surgical procedure is completed.

An instrument I for installing the clenching or clamping device C is shown in FIG. 5 and is designed so that it can be held in one hand by the surgeon. The instrument I includes a main body portion 30 with two openings 32, 34 for accommodating the first two fingers of the surgeon's hand. A slide 36 is adapted to allow the body 30 to move relative to the slide 36 for installing the clenching device C as described below. The slide 36 is formed of a metal rod 38 that is bent at one end to form a loop 40 for accommodating the surgeon's thumb. The other end of the slide 36 is formed with a pair of cooperating and movable chucking pins 42, 44 that are adapted to engage opposite ends of the clenching device C.

A plastic insert 46, positioned within the slide 36, defines the inner side of the thumb opening 40. The insert 46 also includes a ledge 48 that engages the body 30 for limiting the movement of the slide 36 in the direction of arrows 50 when the surgeon's thumb pushes the slide 36 in that direction. The insert 46 also includes a slot 52 in which a safety pin 54 can be inserted to engage a cooperating opening (not shown) in the main body 30 for locking the slide 36 and preventing it from moving relative to the main body 30.

As shown in FIG. 7, when the slide 36 is locked, it engages a clenching device C of the type shown in FIGS. 3 and 4 in its open position as shown in FIG. 3. After the surgeon has installed the anchor A as shown in FIG. 1 and threaded the suture through miniscal cartilage on both sides of the tear T, the suture S is threaded through the openings 26, 28 as shown in FIG. 3, as allowed by a slot 56 formed in the end of the insert 46 adjacent to the chucking pins 42, 44. With the surgeon holding one end of the suture S, the instrument I can be manipulated until the suture S is pulled tight across the tear T and clenching device C is positioned adjacent to the miniscal cartilage 20 as shown in FIG. 1.

When the clenching device is in this position and the suture is as tight as the surgeon wants it to be, the surgeon moves the insert 46 relative to the main body portion 30 in the direction of the arrows 50 by pushing with his or her thumb. This motion operates to close the chucking pins 42, 44 in the direction of arrows 58, to the position shown by the dotted lines in FIG. 5, through the camming action of the metal rod 36 against the inner surface of the main body 30. The chucking pins 42, 44 close the clenching device C by moving the plunger 24 in the tubular body 20 toward the position shown in FIG. 4 for clamping the suture S and holding it tightly in place. The surgeon then pulls back on the insert 46, with his or her thumb, causing the chucking pins 42, 44 to open to the position shown by the solid lines in FIG. 5, so that the surgeon can withdraw the instrument from the incision 12. The incision 12 is then closed in a conventional manner. By clamping the suture in this manner, the need for tying the suture is eliminated, which shortens the surgical procedure and simplifies it.

The anchor A, clenching device C and suture S are all formed of a biodegradable material such as, for example, poly(DL-lactide; a copolymer of glycolide and DL-lactide or L-lactide; a copolymer of caprolactone and DL-lactide or L-lactide; or polycaprolactone. These materials are all absorbable on contact with fluids in animal bodies. Other suitable materials could also be used.

The absorption rate of such materials can be varied by various techniques known in the art such as, for example, exposing the material to gamma radiation for a predetermined length of time for reducing its molecular weight. For the purposes of the invention described above, the anchor, suture and clenching device should all be formed to biodegrade to the point where they cannot hold the tear together after sufficient time to allow the tear to heal; for example, 2-3 months. These materials and techniques for producing them are described in greater detail in U.S. patent application Ser. No. 610,965 filed May 16, 1984, entitled "Biodegradable Prosthetic Device," which is owned by the same entity that owns the subject invention and is incorporated by reference herein as though fully set forth.

As a result of the elements of the invention being formed of such a biodegradable material, they will absorb into the patient's body after the tear T has healed. This results in a surgeon being able to perform the operation described above with only a single surgical procedure since he or she does not have to reopen the wound in order to remove any of the sutures or other apparatus used to repair the tear T.

As a result, an apparatus, method and installer are provided that enable surgery to repair a miniscal tear to be performed more rapidly than previously capable and for making the operation a single surgical step. The installer is easy to use and manipulate and enables the physician to pull the suture tight enough so that the tear T is closed for holding the miniscal cartilage in that position until the tear T can heal.

The foregoing disclosure and description of the invention are illustrative and explanatory thereof, and various changes in the size, shape and materials, as well as in the details of the illustrated construction may be made without departing from the spirit of the invention as defined in the appended claims.

I claim:

1. An apparatus for repairing torn cartilage tissue in a single surgical procedure, comprising:
   (a) a suture;
   (b) anchor means adapted to prevent one end of the suture from being pulled through said cartilage tisue;
   (c) clenching means adapted to hold said suture on the side of the cartilage tissue opposite the anchor means and cooperating with the anchor means for holding the torn tissue together, the suture being held in place with the anchor means and clenching means on opposite side of said tear;
   (d) the suture, anchor means and clenching means being formed of a biodegradable material adapted to be absorbed into an animal body over time for eliminating the need for anotehr surgical procedure to remove than from the animal body after the tear is healed, wherein said clenching means includes:
   a first body member including a first longitudinal opening extending through at least a portion of the body;
   a second body member sized and shaped to releasably fit in said longitudinal opening;
   the first body member including a second radial opening that intersects the first opening and is adapted to receive a suture therethrough when the second body member does not obstruct the second opening;
   the second body member being sized and shaped to clamp the suture when the suture extends through the intersection of the first and second openings and the second body member is moved longitudinally beyond the intersection of the first and second openings.

2. The apparatus of claim 1, wherein:
   the second body member includes a third opening that can be aligned with the second opening for receiving the suture.

3. The apparatus of claim 1, wherein the material of the anchor means suture and clenching means are selected from the group consisting of: poly(DL-lactide); a copolymer of glycolide and DL-lactide or L-lactide; a coplymer of caprolactone and DL-lactide or L-lactide; and polycaprolactone.

4. The apparatus of claim 1, and further including locking means for locking the first and second body members, against relative movement as they hold the suture in place.

5. The apparatus of claim 4, wherein the locking means includes cooperating locking ridges formed on the first and second body portions.

* * * * *